(12) United States Patent
Bosch Navarro et al.

(10) Patent No.: US 8,715,935 B2
(45) Date of Patent: *May 6, 2014

(54) STANDARDIZED METHOD AND KIT FOR THE QUANTIFICATION OF HEPATITIS A VIRUS

(75) Inventors: Albert Bosch Navarro, Barcelona (ES); Rosa María Pintó Solé, Barcelona (ES)

(73) Assignee: Universidad de Barcelona, Barcelona (ES)

( * ) Notice: Subject to any disclaimer, the term of this patent is extended or adjusted under 35 U.S.C. 154(b) by 940 days.

This patent is subject to a terminal disclaimer.

(21) Appl. No.: 12/602,540

(22) PCT Filed: Jun. 1, 2007

(86) PCT No.: PCT/EP2007/055402
§ 371 (c)(1), (2), (4) Date: Dec. 1, 2009

(87) PCT Pub. No.: WO2008/145196
PCT Pub. Date: Dec. 4, 2008

(65) Prior Publication Data
US 2012/0003624 A1   Jan. 5, 2012

(51) Int. Cl.
*C12Q 1/68* (2006.01)
*C07H 21/04* (2006.01)

(52) U.S. Cl.
USPC .... 435/6.12; 435/6.15; 536/24.32; 536/24.33

(58) Field of Classification Search
None
See application file for complete search history.

(56) References Cited

PUBLICATIONS

Costafreda et al. Applied and Environmental Microbiology (2006) 72(6): 3846-3855.*
GenBank Accession No. L22089 (Dec. 5, 2005 [online], [retrieved on Aug. 26, 2012], retrieved from the Internet: <URL:www.ncbi.nlm.nih.gov/nuccore/l22089>.*
Lowe et al. Nucleic Acids Research (1990) 18(7): 1757-1761.*
Jothikumar et al. (Applied and Environmental Microbiology (2005) 71(6): 3359-3363.*
Gregory et al. Applied and Environmental Microbiology (2006) 72(6): 3960-3967.*
Proceedings of the 7th Irish Shellfish Safety Workshop, Nov. 30, 2006, Galway, Ireland.*
Martin et al. Journal of Virology (1996) 70(3): 2027-2031.*
Sanchez et al. Journal of Clinical Microbiology (2002) 40(11): 4148-4155.*
Zhao et al. World Journal of Gastroenterology (2005) 11(4): 508-510.*

* cited by examiner

*Primary Examiner* — Angela M Bertagna
(74) *Attorney, Agent, or Firm* — Young & Thompson

(57) ABSTRACT

The present invention provides a standardized method and a kit for an accurate quantification of HAV in clinical and food samples. The general approach is based on the use of several controls to measure the efficiency of those critical steps of the quantification: the nucleic acids extraction and the RT-PCR reactions. The kit comprises: a Mengo virus mutant strain with the same growth properties than those of the wild-type Mengo virus and with no pathogenic capacity; a single stranded RNA molecule corresponding to a fragment of the HAV genome; primers that specifically bind to regions of the 5' non coding region of the HAV genome; a detectable labeled probe that specifically binds to the amplimer resulting from the RT-PCR; and an appropriate molecule to generate an standard curve for the quantification of HAV.

20 Claims, 3 Drawing Sheets

```
                          SEQUENCE LISTING

<160> NUMBER OF SEQ ID NOS: 15

<210> SEQ ID NO 1
<211> LENGTH: 18
<212> TYPE: DNA
<213> ORGANISM: Artificial Sequence
<220> FEATURE:
<223> OTHER INFORMATION: forward primer HAV68

<400> SEQUENCE: 1
tcaccgccgt ttgcctag                                                     18

<210> SEQ ID NO 2
<211> LENGTH: 19
<212> TYPE: DNA
<213> ORGANISM: Artificial Sequence
<220> FEATURE:
<223> OTHER INFORMATION: reverse primer HAV240

<400> SEQUENCE: 2
ggagagccct ggaagaaag                                                    19

<210> SEQ ID NO 3
<211> LENGTH: 20
<212> TYPE: DNA
<213> ORGANISM: Artificial Sequence
```

```
<220> FEATURE:
<223> OTHER INFORMATION: probe HAV150(-)

<400> SEQUENCE: 3
cctgaacctg caggaattaa                                              20

<210> SEQ ID NO 4
<211> LENGTH: 20
<212> TYPE: DNA
<213> ORGANISM: Artificial Sequence
<220> FEATURE:
<223> OTHER INFORMATION: probe HAV150

<400> SEQUENCE: 4
ttaattcctg caggttcagg                                              20

<210> SEQ ID NO 5
<211> LENGTH: 20
<212> TYPE: DNA
<213> ORGANISM: Artificial Sequence
<220> FEATURE:
<223> OTHER INFORMATION: primer HAV295

<400> SEQUENCE: 5
tgctaatcat ggagttgacc                                              20

<210> SEQ ID NO 6
<211> LENGTH: 24
<212> TYPE: DNA
<213> ORGANISM: Artificial Sequence
<220> FEATURE:
<223> OTHER INFORMATION: primer HAV30BamHI

<400> SEQUENCE: 6
cgggatccct cttggaagtc catg                                         24

<210> SEQ ID NO 7
<211> LENGTH: 51
<212> TYPE: DNA
<213> ORGANISM: Artificial Sequence
<220> FEATURE:
<223> OTHER INFORMATION: primer HAV68BamHI

<400> SEQUENCE: 7
tcaccgccgt tgcctaggc tataggctaa attttcccctt tcggatcccc c            51

<210> SEQ ID NO 8
<211> LENGTH: 26
<212> TYPE: DNA
<213> ORGANISM: Artificial Sequence
<220> FEATURE:
<223> OTHER INFORMATION: reverse primer Mengo209 REV

<400> SEQUENCE: 8
gaagtaacat atagacagac gcacac                                       26

<210> SEQ ID NO 9
<211> LENGTH: 18
<212> TYPE: DNA
<213> ORGANISM: Artificial Sequence
<220> FEATURE:
<223> OTHER INFORMATION: forward primer Mengo110 FW

<400> SEQUENCE: 9
gcgggtcctg ccgaaagt                                                18
```

```
<210> SEQ ID NO 10
<211> LENGTH: 20
<212> TYPE: DNA
<213> ORGANISM: Artificial Sequence
<220> FEATURE:
<223> OTHER INFORMATION: probe Mengo147

<400> SEQUENCE: 10
atcacattac tggccgaagc                                                 20

<210> SEQ ID NO 11
<211> LENGTH: 173
<212> TYPE: DNA
<213> ORGANISM: Artificial Sequence
<220> FEATURE:
<223> OTHER INFORMATION: synthetic primer

<400> SEQUENCE: 11
tcaccgccgt tgcctaggc tataggctaa atttcccttt ccctgtcctt ccctatttc       60 cctttgtttt gtttgtaaat attaattcct gcaggttcag ggttcttaa tctgtttctc    120 tataagaaca ctcaatttc acgctttctg tcttctttct tccagggctc tcc            173

<210> SEQ ID NO 12
<211> LENGTH: 174
<212> TYPE: DNA
<213> ORGANISM: Artificial Sequence
<220> FEATURE:
<223> OTHER INFORMATION: synthetic primer

<400> SEQUENCE: 12
tcaccgccgt tgcctaggc tataggctaa attttcctt tcccttttcc ctttcctatt       60
ccctttgttt tgcttgtaaa tattgattcc tgcaggttca gggttcttaa atctgtttct   120
ctataagaac actcatttt cacgctttct gtcttctttc ttccagggct ctcc            174

<210> SEQ ID NO 13
<211> LENGTH: 155
<212> TYPE: DNA
<213> ORGANISM: Artificial Sequence
<220> FEATURE:
<223> OTHER INFORMATION: synthetic primer

<400> SEQUENCE: 13
tcaccgccgt tgcctaggc tataggctat ttctcccctt cccttttccct gttttgtgta    60 aatattaatt cctgcaggtt cagggttctt aatctgtttt ctctataaga acactcattt   120
tcacgctttc tgtctgcttt cttccagggc tctcc                                155

<210> SEQ ID NO 14
<211> LENGTH: 155
<212> TYPE: DNA
<213> ORGANISM: Artificial Sequence
<220> FEATURE:
<223> OTHER INFORMATION: synthetic primer

<400> SEQUENCE: 14
tcaccgccgt tgcctaggc tttaggctat ttttcccttt ccttccccct gttttgtgta    60
aatattaatt cctgcaggtt caggtttctt aatctgtttt ctctataaga acactcattt   120
tcacgctttc tgtctgcttt cttccagggc tctcc                                155

<210> SEQ ID NO 15
<211> LENGTH: 157
<212> TYPE: DNA
<213> ORGANISM: Artificial Sequence
```

-continued

```
<220> FEATURE:
<223> OTHER INFORMATION: synthetic primer

<400> SEQUENCE: 15
tcaccgccgt tgcctaggc tataggctaa acttcccttt cccctttccc tttattgttg      60
taaatattaa ttcctgcagg ttcagggttc ttggatctgt tccactttat gagcactcat    120
ttcacgcttt ctgtctgctt ttcttccagg gctctcc                             157
```

STANDARDIZED METHOD AND KIT FOR THE QUANTIFICATION OF HEPATITIS A VIRUS

This invention relates to the field of molecular biology and its application in diagnostics. In particular, the invention relates to methods and kits for detecting Hepatitis A virus in clinical, food and environmental samples.

BACKGROUND ART

Hepatitis A virus (HAV) infection is the leading cause of acute viral hepatitis throughout the world. The distribution patterns of hepatitis A in different geographical areas of the world are closely related to their socioeconomic development. The endemicity is low in developed regions and high in underdeveloped countries. HAV infection is mainly propagated via the fecal-oral route, being the person-to-person contact the most common mode of transmission. Its biological cycle displays a viremic phase and an intestinal excretion. Transmission through the parental route may also occur. While in approximately 40% of the reported cases of hepatitis A the source of infection cannot be identified, waterborne and foodborne outbreaks of the disease have been reported. Within this latter category, shellfish grown and harvested from waters receiving urban contaminants is a cause of large outbreaks of infectious hepatitis (cf. M. L. Halliday et al., "An epidemic of hepatitis A attributable to the ingestion of raw clams in Shanghai, China" *J. Infect. Dis.* 1991, vol. 164, pp. 852-9; G. Sanchez et al., "Molecular Characterization of Hepatitis A Virus Isolates from a Transcontinental Shellfish-Borne Outbreak" *J. Clin. Microbiol.* 2002, vol. 40, pp. 4148-55). HAV is a potential contaminant of blood and consequently of hemo-derivatives, and also of bivalve mollusks, fruits and vegetables. It makes necessary the control of its presence in the raw materials and end products of industries of the hemo-derivatives and agro-alimentary sectors.

In the market there are kits for the detection of HAV with different sensitivity. The LightCycler HAV quantification kit from Roche Diagnostics has a sensitivity of 50 genomes/reaction. The RealArt HAV LC RT PCR kit from Qiagen has a sensitivity of 130 international units/ml. Both are only usable with the LightCycler instrument and FRET probes. Other methods for the detection of HAV known in the art are those described in K. H. Abd el Galil et al., "Development of a rapid and quantitative method for the detection of HAV using a combined IMS-molecular beacon-RT-PCR assay", *New Egyptian Journal of Microbiology* 2004, vol. 8, pp. 428-43; and in M. Costa-Mattioli et al., "Quantification and duration of viraemia during hepatitis A infection as determined by real-time RT-PCR", *Journal of viral hepatitis* 2002, vol. 9, pp. 101-6.

Thus, the development of sensitive reliable techniques for the accurate quantification of HAV in the above-mentioned types of samples is required to ensure the safety of these products. In clinics, it is required to prevent transmission of the virus through blood and plasma derivatives or by close personal contact.

SUMMARY OF THE INVENTION

The present invention provides a standardized method for an accurate quantification of HAV in clinical and food samples. The general approach is based on the use of several controls to measure the efficiency of those critical steps of the quantification: the nucleic acids extraction and the RT-PCR reactions. The acronym "RT-PCR" means "reverse transcription polymerase chain reaction" as used commonly in the art.

Accordingly, an aspect of the invention relates to a quantification method of HAV in a sample, by RT-PCR, which comprises the following steps. In a first step, a known concentration of a Mengo virus is added to the sample. This Mengo virus is a mutant strain with the same growth properties than those of the wild-type Mengo virus and with no pathogenic capacity. In a second step, a virus nucleic acids extraction is performed to obtain a nucleic acids suspension, and then at least three subsamples of the nucleic acids suspension are taken. The three subsamples are here referred as 1, 2 and 3. Then, a known concentration of a single stranded RNA (hereinafter referred as ssRNA) molecule which corresponds to a fragment of the HAV genome, is added to the subsample 1. The three subsamples are analyzed by RT-PCR with a reaction mixture comprising primers that specifically bind to regions of the 5' non coding region (5'NCR) of the HAV genome, and a detectable labeled probe that specifically binds to the amplimer resulting from the RT-PCR. For the subsample 3, primers that specifically bind to regions of the Mengo virus that are appropriate to generate an amplimer of the Mengo virus and a detectable labelled probe that specifically binds to the amplimer resulting from the RT-PCR are used. Then, relevant concentrations in each subsample is determined by comparison of the values obtained from the previous analysis with three standard curves, here referred as 1, 2 and 3. The standard curve 1 is used for the quantification of the ssRNA molecule, and is made with the ssRNA molecule titrated by means of the optical density. The standard curve 2 is used for the quantification of HAV, and is made with an appropriate molecule titrated by means of the optical density. The standard curve 3 is used for the quantification of Mengo virus, and is made with Mengo virus titrated by infectivity. Finally, the efficiency of the RT-PCR is determined by comparison of the number of ssRNA molecules detected, by substracting the number of HAV genomes quantified in the subsample 2 from the sum of HAV plus ssRNA molecules in the subsample 1, with the number of ssRNA molecules added. Also, the efficiency of the nucleic acids extraction is determined by comparison of the detected Mengo virus in the subsample 3 with the added Mengo virus.

Another aspect of the invention relates to kits for performing the method defined above, comprising appropriate reagents for the quantification of HAV in a sample.

The method of the invention is highly valuable for the control of the presence and the quantification of HAV in clinical samples (such as blood, sera, plasma and feces), in the source and manufactured blood products and in food (such as shellfish or vegetables). In this latter case it may be very useful in the control of imported food products. The method is also useful in the hemo-derivatives industry for the accurate control of HAV.

It is important not only to detect the presence of HAV but also to quantify the number of virus genomic copies. This is important for instance in clinical samples, where it has been recently described an association between low or very low levels of viremia with fulminant hepatitis (et G. Rezende et al., "Viral and clinical factors associated with the fulminant course of hepatitis A infection", *Hepatology* 2003, vol. 38, pp 613-8), which justifies the need for an extremely sensitive assay. The kit and method of the invention are useful in such serious cases to establish a prognosis of the disease, and to decide the necessity of an hepatic transplant. In blood banks and in the hemo-derivatives industry, the importance is in the detection of the presence of the virus, but the standardized method and kit of the invention provide reliability to avoid false negatives.

Particular embodiments are described below without being limiting of the present invention.

According to the present invention, a non-pathogenic mutant strain of Mengo virus is added as a control of the process of nucleic acids extraction. Mengo virus belongs to the same Picornaviridae family as HAV. Another member of the same family, the encephalomiocarditis virus (EMCV), has been proposed as a model for HAV in validation studies of HAV removal in blood products manufacturing by several agencies such as the European Agency for the Evaluation of Medicinal products or the American Food and Drug Administration. However, the use of this virus is hampered by its potential pathogenicity in several animals, including primates and even man.

In a particular embodiment, the Mengo virus which is used, is the mutant strain $vMC_0$, as described in L. Martin et al., "Mutational analysis of the mengovirus poly(C) tract and surrounding heteropolymeric sequences" *J. Virol.* 1996, vol. 70, pp. 2027-31, which lacks the poly(C) tract from the 5'NCR of the wild-type Mengo virus. This strain has the same growth properties to those of the wild-type virus but with no pathogenic capacity. In addition to its non-pathogenic phenotype, the structure of the chosen target fragment of its 5'NCR makes possible to use the same RT-PCR conditions as for HAV. Thus, the quantification of the Mengo virus and HAV could be performed in the same plate, and under the same program conditions. To further confirm the validity of the Mengo $vMC_0$ strain as a control, a comparison analysis with respect to the behavior of the pHM175 43c HAV strain was performed, and the results demonstrated a similar pattern for both viruses in both sera, fecal and shellfish samples.

HAV is the prototype of the Hepatovirus genus within the Picornaviridae family. Its 7.5-kb single-stranded RNA genome bears different regions: the 5' and 3' NCR, the P1 region which encodes the structural proteins: VP1, VP2, VP3 and a putative VP4, and the P2 and P3 regions encoding non-structural proteins associated with replication. Immunological evidence determines the existence of a single serotype of HAV, although sequencing of the putative VP1/2A junction allows the differentiation of six genotypes, based on nucleotide homologies lower than 85%. However, all six genotypes are very closely related in the 5'NCR, which is the most conserved region of the genome due to its functional structure in the processes of translation and replication, and with a maximum nucleotide divergence of less than 5%. Consequently, the 5'NCR is a very adequate region for the design of an accurate real-time quantification technique. In a particular embodiment of the invention, the primers have sequences which comprise SEQ ID NO: 1 (5'TCACCGCCGTTTGC-CTAG'3, named "HAV68" in the examples) and SEQ ID NO: 2 (5'GGAGAGCCCTGGAAGAAAG'3, "HAV240" in the examples), or their complementary sequences. More particularly, the primers have the sequences SEQ ID NO: 1-2. In another embodiment, the probe has a sequence which comprises SEQ ID NO: 3 (5'CCTGAACCTGCAGGAATTAA'3, "HAV150(−) in the examples). Particularly, the probe has the sequence SEQ ID NO: 3.

The Mengo virus genome copies are titrated by a real-time TaqMan RT-PCR based on the amplification of a fragment of the 5'NCR of the Mengo virus genome. In a particular embodiment of the invention, the primers for Mengo virus have sequences which comprise SEQ ID NO: 8 (5'GAAG-TAACATA TAGACAGACGCACAC3', named "Mengo209 REV" in the examples) and SEQ ID NO: 9 (5'GCGGGTC-CTGCCGAAAGT3', namely "Mengo110 FW" in the examples), or their complementary sequences. More particularly, the primers have the sequences SEQ ID NO: 8-9. The fluorescent probe for the quantification comprises SEQ ID NO: 10 (5'ATCACATTACTGGCCGAAGC3', named "Mengo147" in the examples). Particularly, the probe has the sequence SEQ ID NO: 10.

Currently four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moiety to the same or different oligonucleotide substrates. SYBR Green is a fluorogenic dye that exhibits little fluorescence when in solution, but emits a strong fluorescent signal upon binding to double-stranded DNA. Specific dyes for Taqman are FAM (6-carboxy-fluorescein), VIC and TET (6-carboxy-4,7,2',7'-tetrachloro-fluorescein), which are fluorescent reporter dyes, and TAMRA (6-carboxy-N,N,N',N'-tetramethyl-rhodamine) and MGB (DNA minor groove binder) which are fluorescent and non-fluorescent quencher dyes, respectively. TaqMan probes depend on the 5'-nuclease activity of the DNA polymerase used for PCR to hydrolyze an oligonucleotide that is hybridized to the target amplimer. TaqMan probes are oligonucleotides that have a fluorescent reporter dye attached to the 5' end and a quencher moiety coupled to the 3' end. These probes are designed to hybridize to an internal region of a PCR product. In the unhybridized state, the proximity of the fluor and the quench molecules prevents the detection of fluorescent signal from the probe. During PCR, when the polymerase replicates a template on which a TaqMan probe is bound, the 5'-nuclease activity of the polymerase cleaves the probe. This decouples the fluorescent and quenching dyes and FRET no longer occurs. Thus, fluorescence increases in each cycle, proportional to the amount of probe cleavage. In a particular embodiment of the invention, the probes are labeled with Taqman fluorochromes, and more particularly, the probes are labeled with FAM at the 5' end and is modified with a MGB at the 3' end.

The control of the RT-PCR reaction in the invention relies on a ssRNA molecule corresponding to the viral target and thus amplifiable with the same pair of primers under exactly the same conditions and with the same efficiency. In a particular embodiment of the invention, the ssRNA molecule corresponds to the amplimer of the pHM175 43c strain of Hepatitis A virus with the inclusion of a added restriction site. This is the result of cloning the amplimer under the control of a strong promoter, i.e. the SP6 promoter, which allows the synthesis of huge amounts of RNA transcripts which thereafter will be added at known concentrations to the subsample 1. This amplimer has been modified by the introduction of a new restriction site for the Bam HI enzyme in order to be distinguished from the actual amplimer in case of cross-contaminations. The comparison between the ssRNA titer in genome copies added to the sample and the titer recovered after the RT-PCR enables to verify the efficiency of these reactions, and thus the ssRNA molecule acts as control for the RT-PCR reaction.

In this method, standard curves are constructed from molecules of known concentration. These curves are then used as reference standards for extrapolating quantitative information for molecule targets of unknown concentrations. Spectrophotometric measurements at 260 nm can be used to assess the concentration of the RNA and DNA standards, which can then be converted to a copy number value based on the molecular weight of the nucleic acid used. For the generation of the standard curve for quantification of the target virus (HAV), either the dsDNA molecule corresponding to the actual amplimer, the ssRNA molecule obtained after in vitro transcription of a cloned cDNA corresponding to the amplimer, or the actual virus (pHM175 43c strain) genome could be used. However, the use of either the dsDNA molecule or the actual viral genome is recommended from experimental data. To prevent the manipulation of a viral pathogen, the dsDNA molecule is preferred.

The real-time RT-PCR can be performed in one-step or two-step (see examples below). One-step real-time RT-PCR performs RT and PCR in a single buffer system and in one tube. In two-step RT-PCR, these two steps are performed separately in different tubes. Since the use of a two-step format did not increase the sensitivity of detection, the one-step format is preferred for a less time-consuming and more convenient manipulation, thus reducing cross-contamination risks. In another particular embodiment, the real-time RT-PCR is carried out under the following conditions: 1 hour at 50° C. for the reverse transcription reaction, 10 minutes at 95° C. as a hot start and 45 cycles each of 15 seconds at 95° C. for denaturation, 1 minute at 60° C. for annealing and 1 minute at 70° C. for extension.

In particular embodiments, concentrations of Mengo virus of around $10^5$ infectious units/ml are added in case of clinical samples, sera and stool, while $10^6$ infectious units/g are employed for shellfish samples. Regarding the number of ssRNA molecules, around $10^8$ molecules/ml are preferably to be added in order to minimize a potential competition in case of an HAV-positive sample.

In summary, the whole test involves the generation of three different standard curves: one for the quantification of Mengo virus (made with Mengo virus titrated by infectivity), another for the quantification of the ssRNA molecule control (made with the ssRNA molecule titrated by means of the $OD_{260}$) and a third for the quantification of HAV (made with the dsDNA molecule titrated again by means of the $OD_{260}$). All these standard curves are obtained in a single plate, which additionally contains wells devoted to the calculation of extraction and enzymes efficiencies, as well as the samples to be tested, all under exactly the same conditions.

Another important issue for any diagnostic technique, and particularly when a real-time RT-PCR is evaluated, is its specificity/breadth/sensitivity. The selected targets guarantee an absolute specificity and must reach equilibrium between high sensitivity, broad reactivity and reliability of quantification. The specificity of the proposed primers/probe sequences has been shown to be excellent against a broad panel of enteric viruses, including the other enteric hepatitis virus, i.e. hepatitis E virus, many gastroenteritis viruses, as well as many enteroviruses.

The present invention also provides kits to perform the method of the invention. In particular, a kit comprises: (i) a Mengo virus mutant strain with the same growth properties than those of the wild-type Mengo virus and with no pathogenic capacity; (ii) a ssRNA molecule corresponding to a fragment of the HAV genome; (iii) primers that specifically bind to regions of the 5'NCR of the HAV genome; (iv) a detectable labeled probe that specifically binds to the amplimer resulting from the RT-PCR; (v) primers that specifically bind to regions of the Mengo virus that are appropriate to generate an amplimer of the Mengo virus; (vi) a detectable labelled probe that specifically binds to the Mengo virus amplimer resulting from the RT-PCR; and (vii) an appropriate molecule to generate a standard curve for the quantification of HAV. Particular elements of the kit have been described above in detail. In addition, the kits of the present invention could also comprise other reagents to carry out the method described herein. These include, without limiting, buffers, nucleases-free deionized water, polymerase enzymes, co-factors for an optimal activity of the polymerase enzymes or agents to prevent contamination. A typical PCR master mix may contain a PCR buffer, deoxynucleoside triphosphates, a suitable Taq polymerase and $MgCl_2$. A kit for sample pretreatment can also be included, for instance a RNA extraction kit. The kits of the invention can also include instructions for performing the method described herein and for suitably using the reagents of the kit.

Moreover, the reagents can be provided in a more concentrated form for dilution to the appropriate concentration by the end user.

Unless otherwise defined, all technical and scientific terms used herein have the same meaning as commonly understood by those ordinary skilled in the art. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following particular embodiments, drawings and sequence listing are provided by way of illustration and are not intended to be limiting of the present invention.

DETAILED DESCRIPTION OF PARTICULAR EMBODIMENTS

Cells and Virus

The cytopathogenic pHM175 43c strain of HAV (courtesy of T. Cromeans, Centers for Disease Control, Atlanta, Ga.) was used throughout this study. Virus replication in FRhK-4 cells was performed as previously described (cf. A. Bosch et al., "A new continuous epitope of hepatitis A virus" *J. Med. Virol.* 1998, vol. 54, pp. 95-1022). Infectious Mengo virus was obtained after transfection of a cDNA clone, $pMC_0$ (kindly provided by Prof. Ann Palmenberg, University of Wisconsin), into HeLa cells as previously described (cf. L.

Martin et al., *J. Virol.* 1996, vol. 70, pp. 2027-31), and viral stocks were thereafter produced in the same cells. Additionally a broad collection of enteric viruses, including different members of the Picornaviridae family as well as rotavirus, norovirus, adenovirus, astrovirus and the hepatitis E virus, were tested for their amplification/detection using the HAV-derived primers and probe.

Primer/Probe Set Selection

Figure 1:
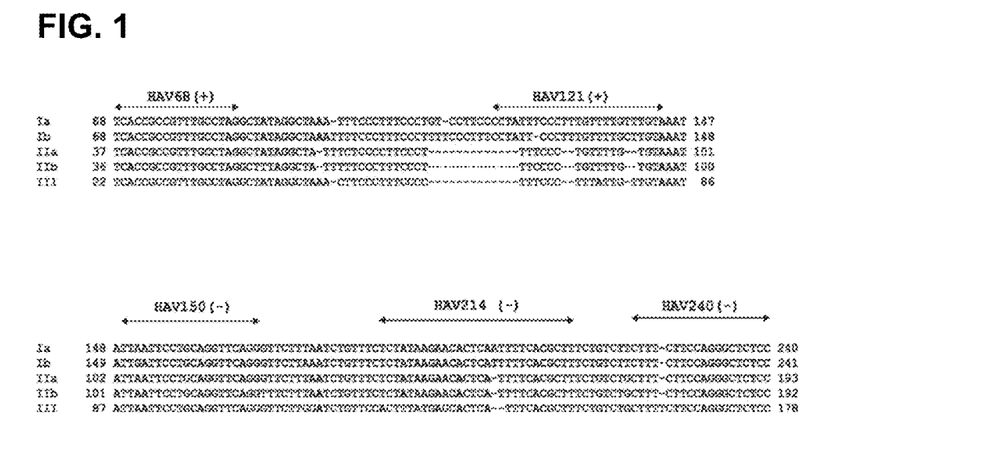
FIG. 1 shows the consensus sequence alignment of human HAV genotypes in the amplified region including the primer and probe target sequences. Nucleotide numbering is made according to the HM-175 strain. Terminal 5' end nucleotides in the available sequences from genotypes II and III are missing.

The selection of a highly conserved primer/probe set was the first step on the design of a real-time RT-PCR for viral quantification. The most conserved region of HAV corresponds to the 5'NCR, being the regions spanning positions 66-95 and 227-262 (numbering corresponds to HM175 strain, accession number M14707) highly conserved. Although some HAV strains include some deletions in the region 99-207, it is otherwise quite well conserved between nucleotides 150-190. A standard RT-PCR-Southern Blot was designed based on the reverse primer HAV240 (5'GGAGAGCCCTGGAAGAAAG3') (SEQ ID NO: 2), the forward primer HAV68 (5'TCACCGCCGTTTGCCTAG3') (SEQ ID NO: 1) and the probe HAV150 (5'TTAATTCCTG-CAGGTTCAGG3') (SEQ ID NO: 4), and proven successful both in serum and shellfish samples. The adaptation of this technique to the real-time format was straightforward. Multiple sequence alignments with the available HAV sequences at the GenBank, including strains belonging to all human genotypes and subgenotypes so far described, were carried out with the ClustalW program (European Bioinformatics Institute). In the HAV240 primer region, the single mutation detected was a point insertion in genotype III (FIG. 1) while in the HAV68 primer region no mutations were observed among the available consensus sequences of the five human genotypes (FIG. 1). Concerning the probe target, a negative strand oligoprobe, HAV150(−) (5'CCTGAACCTGCAG-GAATTAA3') (SEQ ID NO: 3), was synthesized in order to increase the C:G ratio. Finally, the potential loss of sensitivity due to the extended length of the amplified fragment could be amended by modifying the amplification program.

Quasiespecies Analysis of the Primer/Probe Annealing Regions

To further analyze the degree of variability of the target sequences, an analysis of the quasiespecies distribution of the pHM175 43c strain of HAV was undertaken. The pHM175 43c HAV strain was three-times plaque-purified in FRhK-4 cells, as previously described (cf. G. Sanchez et al., *Virology* 2003, vol. 315, pp. 34-42). A biological clone (pHM175 43c P0) was serially passaged 50 times in the same cell line, as previously described (cf. A. Bosch et al., *J. Med. Virol.* 1998, vol. 54, pp. 95-102), and two populations, pHM175 43C P26 and pHM175 43C P50, were analyzed. RNA extracted from both viral populations was retrotranscribed to a cDNA with the M-MLV reverse transcriptase (RT, Roche) using the primer HAV295 (5'TGCTAATCATGGAGTTGACC3') (SEQ ID NO: 5), and the cDNA was copied and amplified by the thermostable Pwo pol (Roche) from *Pyrococcus woesei*, which has proofreading activity, by adding the primer HAV30BamHI (5'CGGGATCCCTCTTGGAAGTC-CATG3') (SEQ ID NO: 6) to the reaction mix. This latter primer incorporates a BamHI restriction site to facilitate its cloning into the pGEM-3Zf(+) vector. The synthesis of the cDNA was performed as previously described (G. Sanchez et al., *Virology* 2003, vol. 315, pp. 34-42). Since the DNA fragments produced by Pwo pol are blunt-ended, a single digestion with the BamHI enzyme was necessary for the amplimer, while the plasmid vector was digested with both BamHI and Hinc II restriction enzymes. Digested DNAs were purified with the High Pure PCR Product Purification Kit (Roche) following the directions of the manufacturer. DNA ligations were performed overnight at 16° C. using T4 DNA ligase (Roche), and transformant clones were screened by the standard white/blue-galactosidase colorimetric reaction. Plasmid DNA from each of 100 clones was purified by using the Wizard Plus SV Minipreps Kit (Promega). Nucleotide sequencing was carried out in an ABI PRISM 377 automated DNA sequencer, with the ABI PRISM BigDye Terminator v3.1 Cycle Sequencing Kit (Applied Biosystems) and using vector-derived primers. All mutations were confirmed by sequencing both strands of DNA. Regarding the target sequences for the HAV240 reverse primer, no mutations were detected neither at P26 or P50. The number of mutations found in the forward primer region was of one at P50 in the HAV68 target sequence. Finally, the target region for the probe showed a point mutation at P50. This low level of variability ensures the robustness of the assay.

Specificity of the Chosen Primer/Probe Set

In order to confirm the specific detection of HAV, a wide variety of enteric viruses were tested for their amplification/detection by using the HAV240, HAV68/HAV150 primers/probe set. The assayed viruses included ten different picornaviruses: Poliovirus (serotype 1 vaccinal strain), Human Enterovirus B (Echovirus 1), Human Enterovirus B (Echovirus 11), Human Enterovirus B (Echovirus 30), Human Enterovirus B (Coxackievirus-B5), Human Enterovirus C (Coxackievirus-A24), Human Enterovirus D (Enterovirus 70), Bovine Enterovirus, Porcine teschovirus (Porcine Enterovirus 1) and Encephalomyocarditis virus. Other enteric viruses such as Hepatitis E virus, human and porcine Rotavirus (group A), Norovirus (Norwalk-like virus), Mamastrovirus (human astrovirus type 1) and Human adenovirus F (enteric adenovirus type 40) were also employed. As expected, none of the tested virus resulted positive either at high concentration ($10^6$ to $10^8$ $TCID_{50}$/ml or undiluted 10% fecal suspensions) or low concentration ($10^4$ $TCID_{50}$/ml or 1/10 dilutions of 10% fecal suspensions). The HAV strain pHM175 43c, belonging to genotype IB, was used as positive control. These data ensures the high specificity of the assay.

Best Standard Molecules for the Generation of the Standard Curves

Figure 2:
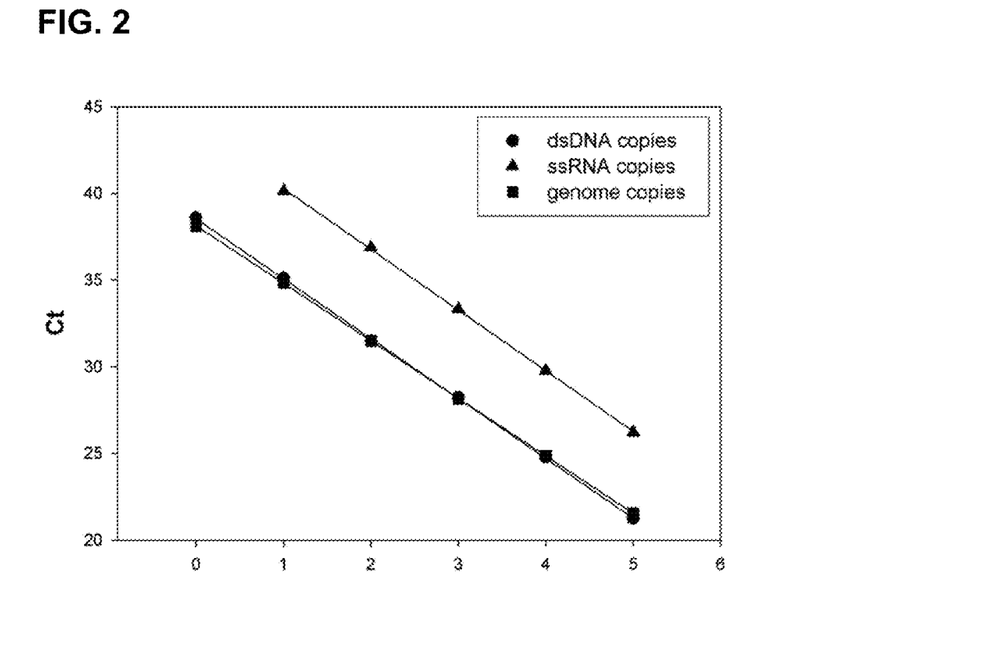
FIG. 2 shows the standard curves for the HAV real-time TaqMan RT-PCR assay. Three molecules were employed: a dsDNA, a ssRNA and the pHM175 43c strain viral genome. The concentration of the synthetic molecules was estimated by determining the $OD_{260}$. Virus titer was determined by infectivity and physical genomes estimated by applying a 60× factor to the infectious titer.

One of the crucial steps in a real-time quantification is the choice of the most proper molecule for the generation of the standard curve. Three candidates exist being able to be amplified and detected by means of the selected primers and probe, and whose concentration may be determined: a dsDNA molecule corresponding to the actual amplimer, a ssRNA molecule obtained after an in vitro transcription of a cloned cDNA corresponding to the amplimer and the actual virus (pHM175 43c strain) genome. The concentration of each of these molecules was estimated by determining the $OD_{260}$ in the two former cases and by infectivity in the third case. In this latter case, however, the final concentration was refined by applying a 60× factor to the infectious titer in order to achieve a reliable number of physical genomes. As an example, a representative set of standard curves for a one-step TaqMan reaction is depicted in FIG. 2. The estimated regression lines for the dsDNA, ssRNA and viral genome molecules in distilled water were y=38.56-3.46×($r^2$=0.999), y=43.75-3.50×($r^2$=0.999) and y=38.13-3.32×($r^2$=0.999), respectively (FIG. 2). Although the slopes of the three curves are similar, the intercept value in the case of the ssRNA molecule is significantly higher. From these results it is advisable to recommend the use either of the dsDNA molecule or the actual viral genome for the construction of the standard curve. Using the pHM175 43c strain, a linear range of detection from 1 physical particle/reaction or 200 physical particles/ml to $10^5$ physical particles/reaction or $2\times10^7$ physical particles/ml was achieved. With the dsDNA molecule the upper limit was extended to at least $2\times10^{10}$ molecules/ml.

Limit of Detection for Different Real-Time RT-PCR Formats

Two real-time RT-PCR formats based on the detection of amplimers through two different fluorogenic chemistries were assayed for the development of a HAV quantification technique. A TaqMan probe on the one hand and a beacon probe on the other were assayed. Additionally, in the case of the TaqMan probe, several one-step and two-step formats were also evaluated. In each case standard curves using the ssRNA molecule, the dsDNA amplimer and the actual virus were drawn. Once optimized, i.e., adjusting primers and probe concentration for each kit, all of them gave very good detection limits in both one- and two-step formats (10 ssRNA molecules, 1 viral RNA molecule and 0.05 infectious viruses per reaction), with the sole exception of the Applied Biosystems one-step kit which showed a significantly lower sensitivity. However the beacon probe format was neither as sensitive nor as reproducible as the TaqMan probe format (10 ssRNA molecules, 10 viral RNA molecules and 0.5 infectious viruses per reaction). Since the use of a two-step format did not increase the sensitivity of detection, the one-step format is recommended for a less time-consuming and more convenient manipulation, thus reducing cross-contamination risks.

Real-Time RT-PCR TagMan Assays

The TaqMan probe was labeled with 6-carboxy-fluorescein (FAM) at the 5' end and was modified with a minor groove binder (MGB) at the 3' end. The real-time instruments used were the ABI PRISM 7700 (Applied Biosystems) and the Mx3000P (Stratagene). The one-step Brilliant QRT-PCR Core Reagent kit from Stratagene and a two-step assay with a home-designed RT reaction combined with the FullVelocity QPCR Master Mix from Stratagene and the Mx3000P apparatus were employed for the development of the technique. For the one-step reaction, the concentration of primers, probe, and $Mg^{2+}$ was optimized at 0.6 μM, 0.25 μM, and 3 mM, respectively, in a final volume of 25 μl containing 5 μl of sample. The temperature-time-program was as follows: 1 hour at 50° C. for the RT reaction, 10 min at 95° C. as a hot start and 45 cycles each of 15 sec at 95° C. for denaturation, 1 min at 60° C. for annealing and 1 min at 70° C. for extension. The fluorescence was measured at the end of each cycle. In the two-step assay the RT reaction was performed at 45° C. for 1 hour, using the Expand Reverse Transcriptase (Roche) with 0.5 μM of the reverse primer, 0.2 mM of nucleotides and 5 mM of DTT in a final volume of 25 μl containing 10 μl of sample. The optimized composition for the PCR mix using the FullVelocity QPCR kit was 0.9 μM of the reverse primer, 0.5 μM of the forward primer and 0.25 μM of probe in a final volume of 25 μl in which 5 μl of the RNA template has been added. The amplification program consisted of preheating for 2 min at 95° C. and 40 cycles of 10 sec at 95° C. for denaturation and 1 min at 60° C. for annealing-extension. The fluorescence was read at the end of each cycle.

Construction of a RNA Standard

A synthetic RNA molecule to be used as a control standard was obtained by in vitro transcription of a cloned cDNA corresponding to the amplimer resulting from the RT-PCR with the reverse primer HAV240 (SEQ ID NO: 2) and the forward primer HAV68BamHI (5'TCACCGCCGTTTGC-CTAGGCTATAGG CTAAATTTTCCCTTTCGGATC-CCCC3') (SEQ ID NO: 7) of the pHM175 43c HAV strain. This amplimer corresponds to the one synthesized in the real-time techniques hereby presented but including a newly generated BamHI restriction site in order to be distinguished from the viral amplimer in case of cross-contamination. The cloned amplimer was synthesized in an RT-PCR with the Expand RT enzyme and the Pwo DNA polymerase (Roche) which generates blunt-ended termini. The pGEM-3Zf(+) vector was digested with the enzyme HincII. After purification, both amplimer and vector were overnight ligated at 16° C. using T4 DNA ligase. Ligation products were transformed in E. coli DH5α, and transformant clones were screened by the standard white/blue-galactosidase colorimetric reaction. Several positive clones were analyzed and one containing the cDNA under the control of the SP6 polymerase was selected. The in vitro transcription was performed on linearized plasmid samples using the Riboprobe in vitro transcription System-SP6 kit (Promega) following the manufacturer's instructions. The concentration of RNA transcripts was measured by OD260 after their purification with the RNeasy Plant mini kit (QIAGEN) following the recommended procedure.

Best Standard Molecules for Accurate Quantification

A one-step TaqMan real-time RT-PCR based on the amplification of a related 5'NCR fragment from the Mengo virus genome was developed and optimized for the working conditions of the HAV assay, in order to be quantified in the same plate. The selection of a highly conserved primer/probe set was the first step on the design of a real-time RT-PCR for viral quantification. The most conserved region of Mengo virus corresponds to the 5'NCR and primers and probe for the real-time RT-PCR were chosen from this region. The reverse primer Mengo209 REV (5'GAAGTAACATATAGACA-GACGCACAC3') (SEQ ID NO: 8) and the forward primer Mengo110 FW (5'GCGGGTCCTGCCGAA AGT3') (SEQ ID NO: 9) were used for the RT-PCR amplification. The fluorescent probe for the quantification was the Mengo147 (5'ATCACATTACT GGCCGAAGC3') (SEQ ID NO: 10) labeled with the 5'6-carboxyfluorescein (FAM) and modified with a 3' minor groove binder (MGB).

The sensitivity of this technique was of 100 physical particle/reaction with a linear range from $2.0\times10^2$ to $2.0\times10^9$ particles/ml.

Figure 3:
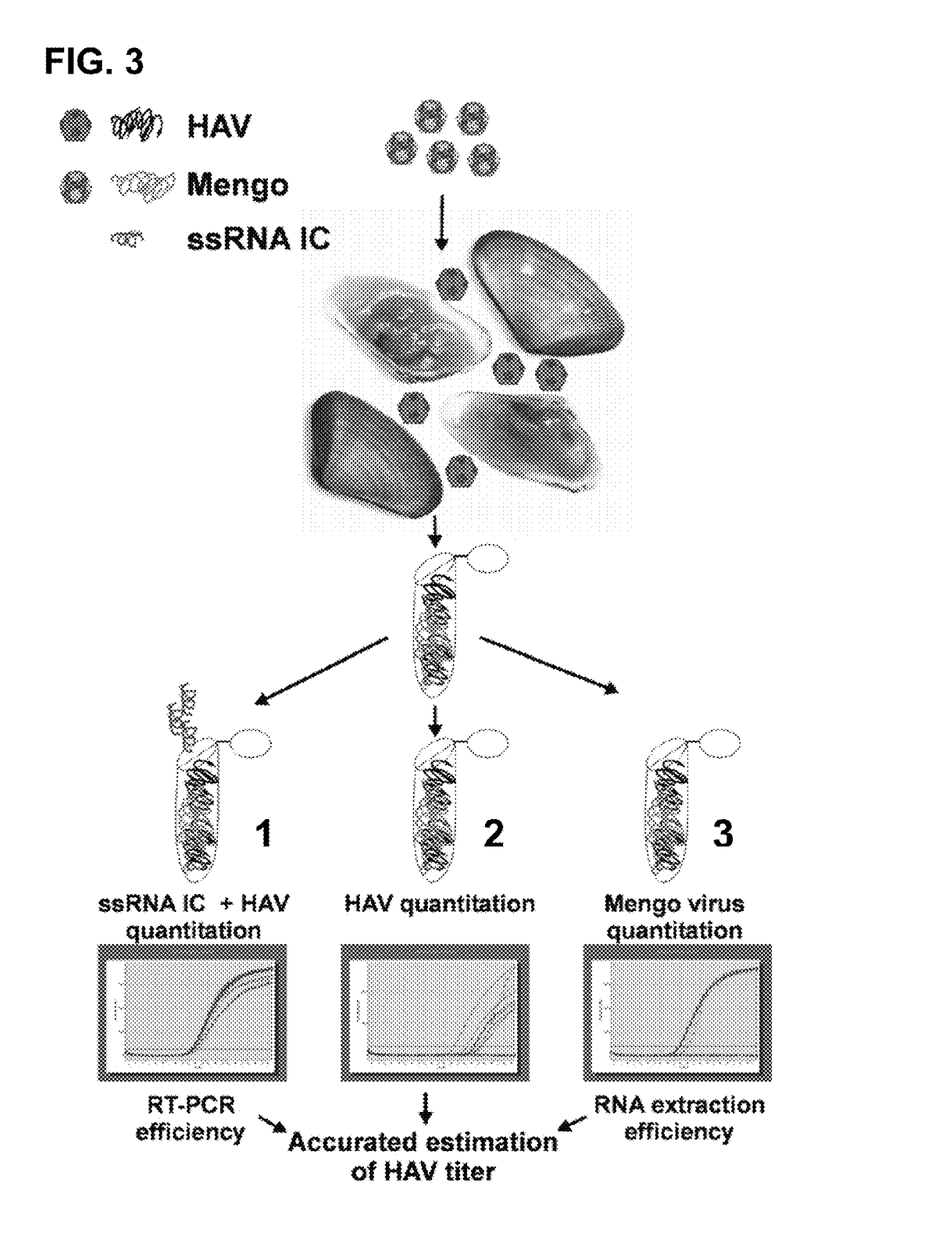
FIG. 3 shows the proposed standardized procedure for an accurate estimation of HAV genome copies in food or clinical samples. 1, 2 and 3 refer to the three subsamples and also to the corresponding standard curves.

A schematic representation of the whole control process is shown in FIG. 3. This approach consists of the addition of a known concentration of Mengo virus to the sample to be analyzed, before performing the virus nucleic acids extraction. Once the extraction is performed, three separate subsamples of the nucleic acids suspension are analyzed. In one subsample a known concentration of the ssRNA control is added. In two of the subsamples, including the one with the ssRNA control, quantification of HAV is performed. In the third subsample, quantification of Mengo virus is assessed. Two values will be obtained for HAV, corresponding to the level of virus present in the sample on the one hand, and to the addition of the HAV genomes plus the ssRNA molecules on the other. At this point the efficiency of the RT-PCR reaction may be estimated by comparing the number of ssRNA molecules detected (by substracting the number of HAV genomes quantified in one subsample from the sum of HAV plus ssRNA in the other subsample) with the number of ssRNA molecules added. Finally from the third subsample, the efficiency of the nucleic acids extraction may be calculated by comparing the detected and added Mengo virus genomes.

Altogether an accurate estimation of the numbers of HAV genomes present in a given sample may be achieved. However, important issues must be solved before conducting the whole test: the determination of the optimal amount of Mengo virus to be added. Three different concentrations of Mengo virus were tested in serum, stool suspensions and shellfish digestive tissues (TABLE 1), ranging from $8.6\times10^6$ to $8.6\times10^2$ infectious units/ml in the two former cases and from $1.0\times10^6$ to $1.0\times10^2$ infectious units/g of digestive tissues in the third type of sample. Each spiked sample was extracted twice and each nucleic acids suspension was titrated by real-time TaqMan RT-PCR. Although a certain level of variability was observed in all types of samples, this variability was indeed more related to the nature of the particular samples rather than to the concentration of viruses added. In view of the low viral nucleic acids recovery efficiencies (TABLE 1), mostly in shellfish samples, concentrations of Mengo virus of around $10^5$ infectious units/ml were selected for clinical samples, sera and stool, while $10^6$ infectious units/g were employed for shellfish samples. In an attempt to discard the possibility of a different behavior of Mengo virus and HAV during the extraction procedures a comparative experiment was performed in which the pHM175 43c strain of HAV was added at different concentrations to the different types of samples (TABLE 2). The extraction efficiency was similar for both viruses thus validating the use of the Mengo virus control.

Regarding the number of ssRNA molecules a rather high concentration (around $10^8$ molecules/ml) was added in order to minimize a potential competition in case of an HAV-positive sample. This complete approach was applied to the quantification of experimentally contaminated clinical and shellfish samples as well as to naturally contaminated clinical and shellfish samples.

Clinical Samples, Shellfish Samples and Viral RNA Extraction

Clinical samples included stool and sera samples from patients affected of hepatitis A. Additionally, stool and sera samples from patients non-affected of hepatitis A were experimentally contaminated with the pHM175 43c HAV strain. Stools were suspended (10%, wt/vol) in phosphate-buffered saline containing 2M $NaNO_3$, 1% BSA (FractionV) and 0.1% Triton X-100 (pH 7.2), pelleted at 1000×g for 5 min, and nucleic acids extracted from 150 µl of the resulting supernatant using the RNeasy Plant Mini Kit (QIAGEN). Nucleic acids were purified from 150 µl of serum by using the NucleoSpin RNA Virus (Macherey-Nagel). Frozen samples of clams directly associated with an outbreak of hepatitis A, were analyzed. Processing of shellfish was performed essentially by the method described by Atmar et al (cf. R. L. Atmar et al., "Detection of Norwalk virus and hepatitis A virus in shellfish tissues with the PCR" *Appl. Environ. Microbiol.* 1995, vol. 61, pp. 3014-8). Briefly, the stomachs and digestive diverticula were dissected from the clams and subjected to high-speed homogenization (Sorval OCI Omni mixer, Omni Intl., Waterbury, Conn., USA). Viruses were extracted from the homogenates (corresponding to 1.5 g of shellfish tissue) by sequential extractions with chloroform-butanol and Cat-Floc T (Calgon Corp., Elwood, Pa., USA), and concentrated by polyethylene-glycol precipitation. Nucleic acids from these concentrates were extracted with the RNeasy Plant Mini Kit (QIAGEN) following the manufacturer's instructions. RNA extraction from viruses harvested from cell cultures was performed with the NucleoSpin RNA Virus (Macherey-Nagel).

HAV Quantification in Clinical Samples

Figure 4:
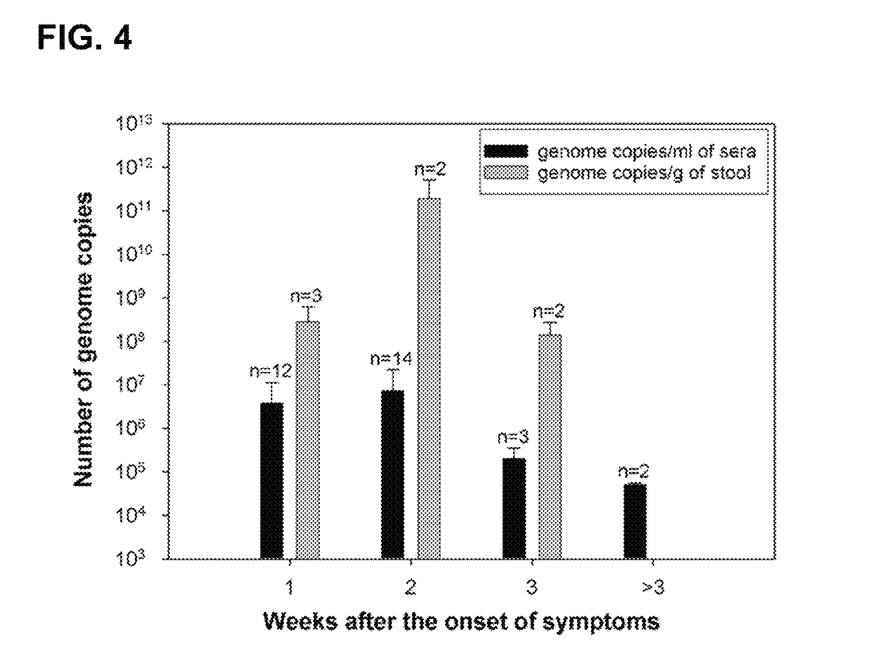
FIG. 4 shows the time-course of HAV genome copies in sera and feces from patients of a shellfish-borne outbreak.

This complete approach was applied for the quantification of HAV in clinical samples from patients suffering from acute hepatitis and diagnosed positive for hepatitis A by means of IgM positivity. Only samples belonging to genotypes IA (sporadic cases) and IB (shellfish-borne outbreak) were available. In this latter case, the quantitative results (TABLE 3) revealed a high and long lasting viremia, with the peak occurring at two weeks after the onset of symptoms (FIG. 4). Although for genotype IA samples no information was available about the moment in which the sera was obtained, assuming that the most probable situation is around one to two weeks, no significant differences in the number of genome copies per ml was observed with regard to genotype IB, with the exception of sample 2. This latter sample showed a significantly higher number of HAV genomes, clearly exceeding even the average detected at two weeks post-symptoms. However, it should be mentioned that this sample belonged to an HIV-positive patient. Regarding the titers detected in feces, the results revealed numbers higher than expected (TABLE 4) with a peak showing up again around two weeks after the onset of symptoms (FIG. 4).

HAV Quantification in Shellfish Samples

The same approach was applied for the quantification of the HAV present in the shellfish samples associated with the above mentioned outbreak (TABLE 5). Three out of seven tested samples could be quantified, showing estimated titers ranging from $7.5 \times 10^3$ to $7.3 \times 10^5$ HAV genomes per gram of digestive tissues, or around $1 \times 10^3$ to $1 \times 10^5$ per g of clam. The rest of the samples, were either negative for viruses or contained virus levels below the detection limit, which strongly depends on the efficiency of the extraction procedure.

TABLE 1

Validation of Mengo virus and ssRNA control as standards for the determination of nucleic acids extraction and RT-PCR efficiencies, respectively.

| Sample | Spiked Mengo Virus[a] | Recovered Mengo Virus[b] | NA Extraction Efficiency (%) | Spiked ssRNA[c] | Recovered ssRNA[d] | RT-PCR Efficiency (%) |
|---|---|---|---|---|---|---|
| Serum-1 | $8.6 \times 10^6$ | $(1.1 \pm 1.4) \times 10^7$ | $100.0 \pm 0.0$ | $1.2 \times 10^8$ | $(2.5 \pm 1.0) \times 10^8$ | $100.0 \pm 0.0$ |
| | $8.6 \times 10^4$ | $(3.6 \pm 1.0) \times 10^5$ | $100.0 \pm 0.0$ | $1.2 \times 10^8$ | $(2.0 \pm 0.6) \times 10^8$ | $100.0 \pm 0.0$ |
| | $8.6 \times 10^2$ | $(3.6 \pm 2.3) \times 10^3$ | $100.0 \pm 0.0$ | $1.2 \times 10^8$ | $(2.1 \pm 1.3) \times 10^8$ | $100.0 \pm 0.0$ |
| Serum-2 | $8.6 \times 10^6$ | $(1.1 \pm 3.7) \times 10^6$ | $12.3 \pm 4.4$ | $1.6 \times 10^8$ | $(1.9 \pm 0.5) \times 10^8$ | $100.0 \pm 0.0$ |
| | $8.6 \times 10^4$ | $(2.5 \pm 1.6) \times 10^4$ | $28.8 \pm 19.0$ | $1.6 \times 10^8$ | $(2.8 \pm 0.4) \times 10^8$ | $100.0 \pm 0.0$ |
| | $8.6 \times 10^2$ | $(2.6 \pm 1.9) \times 10^2$ | $30.7 \pm 21.7$ | $1.6 \times 10^8$ | $(1.6 \pm 0.3) \times 10^8$ | $93.5 \pm 9.2$ |
| Stool-1 | $8.6 \times 10^6$ | $(3.4 \pm 0.4) \times 10^6$ | $39.5 \pm 4.9$ | $1.2 \times 10^8$ | $(2.2 \pm 1.7) \times 10^7$ | $18.1 \pm 14.3$ |
| | $8.6 \times 10^4$ | $(5.1 \pm 2.2) \times 10^4$ | $59.0 \pm 25.4$ | $1.2 \times 10^8$ | $(9.6 \pm 0.2) \times 10^6$ | $8.3 \pm 1.8$ |
| | $8.6 \times 10^2$ | $(4.3 \pm 2.3) \times 10^2$ | $49.3 \pm 25.9$ | $1.2 \times 10^8$ | $(1.5 \pm 0.8) \times 10^7$ | $12.3 \pm 6.6$ |
| Stool-2 | $8.6 \times 10^6$ | $(3.0 \pm 1.3) \times 10^6$ | $34.6 \pm 15.3$ | $1.6 \times 10^8$ | $(3.1 \pm 0.3) \times 10^8$ | $100.0 \pm 0.0$ |
| | $8.6 \times 10^4$ | $(3.5 \pm 6.6) \times 10^3$ | $40.0 \pm 7.6$ | $1.6 \times 10^8$ | $(3.4 \pm 0.8) \times 10^8$ | $100.0 \pm 0.0$ |
| | $8.6 \times 10^2$ | $(9.3 \pm 10.0) \times 10^2$ | $65.7 \pm 48.4$ | $1.6 \times 10^8$ | $(1.6 \pm 0.6) \times 10^8$ | $100.0 \pm 0.0$ |
| Shellfish | $1.0 \times 10^6$ | $(9.1 \pm 9.2) \times 10^2$ | $0.1 \pm 0.1$ | $1.5 \times 10^8$ | $1.3 \pm 0.4 \times 10^8$ | $84.3 \pm 21.4$ |
| | $1.0 \times 10^4$ | $(2.2 \pm 0.7) \times 10^1$ | $0.2 \pm 0.1$ | $1.5 \times 10^8$ | $(1.2 \pm 0.3) \times 10^8$ | $79.9 \pm 17.5$ |
| | $1.0 \times 10^2$ | ND[e] | — | $1.5 \times 10^8$ | $(1.6 \pm 0.4) \times 10^8$ | $93.2 \pm 6.7$ |

[a]The inocula added are expressed as $TCID_{50}$/ml for sera and stool suspensions, or $TCID_{50}$/g of hepatopancreas for shellfish.
[b]Each spiked sample was extracted twice and each nucleic acids suspension was titrated by real-time TaqMan RT-PCR using a standard curve made by means of Mengo virus infectious units.
[c]The inocula added are expressed as the number of molecules of the ssRNA control per ml of nucleic acids suspension.
[d]Each spiked nucleic acids suspension was titrated by a TaqMan Real-time RT-PCR using a standard curve made by means of HAV-derived ssRNA molecules estimated from the $OD_{260}$ readings.
[e]ND: Not detected.

TABLE 2

Comparative behavior of infectious Mengo virus and infectious HAV in the nucleic acids extraction.

| Sample | Spiked Mengo Virus[a] | Recovered Mengo Virus[b] | NA Extraction Efficiency (%) | Spiked HAV[c] | Recovered HAV[d] | NA Extraction Efficiency (%) |
|---|---|---|---|---|---|---|
| Serum-1 | $8.6 \times 10^6$ | $1.3 \times 10^5$ | 1.5 | $2.0 \times 10^6$ | $1.1 \times 10^5$ | 5.5 |
|  | $8.6 \times 10^4$ | $1.0 \times 10^4$ | 11.6 | $2.0 \times 10^4$ | $6.7 \times 10^2$ | 3.3 |
| Stool | $8.6 \times 10^6$ | $2.1 \times 10^6$ | 23.8 | $2.0 \times 10^6$ | $2.8 \times 10^5$ | 14.0 |
|  | $8.6 \times 10^4$ | $3.0 \times 10^4$ | 34.6 | $2.0 \times 10^4$ | $1.4 \times 10^3$ | 7.0 |
| Shellfish | $1.0 \times 10^6$ | $1.6 \times 10^3$ | 0.2 | $2.0 \times 10^6$ | $4.0 \times 10^3$ | 0.2 |
|  | $1.0 \times 10^4$ | $2.7 \times 10^0$ | 0.3 | $2.0 \times 10^4$ | $3.3 \times 10^1$ | 0.2 |

[a]The inocula added are expressed as $TCID_{50}$/ml for sera and stool suspensions, or $TCID_{50}$/g of hepatopancreas for shellfish.
[b]Each spiked sample was extracted and the nucleic acids suspension titrated by real-time TaqMan RT-PCR using a standard curve made by means of Mengo virus infectious units.
[c]The pHM175 43c strain of HAV was added and virus titers are expressed as $TCID_{50}$/ml for sera and stool suspensions, or $TCID_{50}$/g for shellfish.
[d]Each spiked sample was extracted and the nucleic acids suspension titrated by real-time TaqMan RT-PCR using a standard curve made by means of HAV infectious units.

TABLE 3

Quantification of HAV in sera samples from patients infected with either genotype IA or IB. IB samples belong to different patients from an outbreak.

| Sample Genotype | Spiked Mengo Virus[a] | R. Mengo Virus[b] | NA E.E (%) | Spiked ssRNA[c] | R. ssRNA[d] | RT-PCR Efficiency (%) | HAV Crude Sample[e] | HAV Final Estimate[e] |
|---|---|---|---|---|---|---|---|---|
| 1 (IA) | $1.3 \times 10^5$ | $3.2 \times 10^4$ | 24.7 | $1.5 \times 10^8$ | $1.6 \times 10^8$ | 100.0 | $1.6 \times 10^5$ | $6.4 \times 10^5$ |
| 2 (IA) | $1.3 \times 10^5$ | $5.4 \times 10^4$ | 51.9 | $1.5 \times 10^8$ | $1.4 \times 10^8$ | 94.1 | $3.2 \times 10^8$ | $6.2 \times 10^8$ |
| 3 (IA) | $1.3 \times 10^5$ | $5.7 \times 10^4$ | 48.5 | $1.5 \times 10^8$ | $1.5 \times 10^8$ | 98.2 | $3.2 \times 10^7$ | $6.6 \times 10^7$ |
| 1 (IB) (1 week[f]) | $1.3 \times 10^5$ $1.3 \times 10^5$ | $6.6 \times 10^4$ | 50.0 | $1.5 \times 10^8$ | $2.3 \times 10^8$ | 100.0 | $4.8 \times 10^5$ | $9.6 \times 10^5$ |
| 2 (IB) (1 week) | $1.3 \times 10^5$ | $1.7 \times 10^4$ | 13.0 | $1.5 \times 10^8$ | $2.6 \times 10^8$ | 100.0 | $1.4 \times 10^5$ | $1.1 \times 10^6$ |
| 3 (IB) (2 weeks) | $1.3 \times 10^5$ | $6.6 \times 10^3$ | 5.0 | $1.5 \times 10^8$ | $1.9 \times 10^8$ | 100.0 | $1.9 \times 10^6$ | $3.8 \times 10^7$ |
| 4 (IB) (2 weeks) | $1.3 \times 10^5$ | $1.5 \times 10^4$ | 11.5 | $1.5 \times 10^8$ | $1.2 \times 10^8$ | 78.4 | $9.2 \times 10^5$ | $8.0 \times 10^6$ |
| 5 (IB) (3 weeks) | $1.3 \times 10^5$ | $1.7 \times 10^4$ | 13.0 | $1.5 \times 10^8$ | $1.4 \times 10^8$ | 94.1 | $7.4 \times 10^4$ | $5.6 \times 10^5$ |
| 6 (IB) (3 weeks) | $1.3 \times 10^5$ | $3.8 \times 10^4$ | 28.5 | $1.5 \times 10^8$ | $1.8 \times 10^8$ | 100.0 | $6.8 \times 10^4$ | $2.4 \times 10^5$ |
| 7 (IB) (6 weeks) | $1.3 \times 10^5$ | $8.6 \times 10^3$ | 6.5 | $1.5 \times 10^8$ | $1.4 \times 10^8$ | 94.1 | $3.1 \times 10^3$ | $4.8 \times 10^4$ |
| 8 (IB) (6 weeks) | $1.3 \times 10^5$ | $6.3 \times 10^4$ | 48.5 | $1.5 \times 10^8$ | $2.1 \times 10^8$ | 100.0 | $2.6 \times 10^4$ | $5.4 \times 10^4$ |

R. means recovered.
E.E. means Extraction Efficiency.
[a]The inocula added are expressed as $TCID_{50}$/ml of serum.
[b]Each spiked sample was extracted and the nucleic acids suspension was titrated by real-time TaqMan RT-PCR using a standard curve made by means of Mengo virus infectious units.
[c]The inocula added are expressed as the number of molecules of the ssRNA control per ml of nucleic acids suspension.
[d]Each spiked nucleic acids suspension was titrated by a TaqMan Real-time RT-PCR using a standard curve made by means of HAV-derived ssRNA molecules estimated from the $OD_{260}$ readings.
[e]The titer is expressed as the number of genome copies per ml of serum.
[f]Week after the onset of symptoms at which the samples were taken.

TABLE 4

Quantification of HAV in fecal samples from patients with acute hepatitis A from a genotype IB outbreak.

| Sample | Spiked Mengo Virus[a] | R. Mengo Virus[b] | NA E.E. (%) | Spiked ssRNA[c] | R. ssRNA[d] | RT-PCR Efficiency (%) | HAV Crude Sample[e] | HAV Final Estimate[e] |
|---|---|---|---|---|---|---|---|---|
| 1 (1 week[f]) | $1.3 \times 10^5$ | $2.8 \times 10^4$ | 21.0 | $1.5 \times 10^8$ | $9.6 \times 10^7$ | 64.9 | $1.1 \times 10^7$ | $5.1 \times 10^8$ |
| 2 (1 week) | $1.3 \times 10^5$ | $2.7 \times 10^3$ | 2.1 | $1.5 \times 10^8$ | $5.2 \times 10^7$ | 35.1 | $9.2 \times 10^4$ | $4.4 \times 10^7$ |
| 3 (1 week) | $1.3 \times 10^5$ | $3.5 \times 10^4$ | 26.5 | $1.5 \times 10^8$ | $1.3 \times 10^7$ | 8.6 | $3.6 \times 10^4$ | $4.2 \times 10^6$ |
| 4 (2 week) | $1.3 \times 10^5$ | $8.0 \times 10^3$ | 6.0 | $1.5 \times 10^8$ | $1.0 \times 10^6$ | 1.0 | $2.2 \times 10^7$ | $2.2 \times 10^{10}$ |
| 5 (2 week) | $1.3 \times 10^5$ | $1.3 \times 10^3$ | 1.0 | $1.5 \times 10^8$ | $1.0 \times 10^8$ | 70.3 | $5.6 \times 10^7$ | $5.6 \times 10^{11}$ |

TABLE 4-continued

Quantification of HAV in fecal samples from patients with acute hepatitis A from a genotype IB outbreak.

| Sample | Spiked Mengo Virus[a] | R. Mengo Virus[b] | NA E.E. (%) | Spiked ssRNA[c] | R. ssRNA[d] | RT-PCR Efficiency (%) | HAV Crude Sample[e] | HAV Final Estimate[e] |
|---|---|---|---|---|---|---|---|---|
| 6 (3 week) | $1.3 \times 10^5$ | $2.8 \times 10^3$ | 2.1 | $1.5 \times 10^8$ | $2.0 \times 10^7$ | 21.6 | $5.6 \times 10^5$ | $2.7 \times 10^8$ |
| 7 (3 week) | $1.3 \times 10^5$ | $5.1 \times 10^4$ | 38.0 | $1.5 \times 10^8$ | $9.6 \times 10^6$ | 6.5 | $4.6 \times 10^4$ | $7.1 \times 10^6$ |

R. means recovered.
E.E. means Extraction Efficiency.
[a]The inocula added are expressed as $TCID_{50}$/ml of fecal suspension.
[b]Each spiked sample was extracted and the nucleic acids suspension was titrated by real-time TaqMan RT-PCR using a standard curve made by means of Mengo virus infectious units.
[c]The inocula added are expressed as the number of molecules of the ssRNA control per ml of nucleic acids suspension.
[d]Each spiked nucleic acids suspension was titrated by a TaqMan Real-time RT-PCR using a standard curve made by means of HAV-derived ssRNA molecules estimated from the $OD_{260}$ readings.
[e]The titer is expressed as the number of genome copies per g of feces.
[f]Week after the onset of symptoms at which the samples were taken.

TABLE 5

Quantification of HAV in shellfish samples associated with a genotype IB outbreak.

| Sample | Spiked Mengo Virus[a] | R. Mengo Virus[b] | NA E.E. (%) | Spiked ssRNA[c] | R. ssRNA[d] | RT-PCR Efficiency (%) | HAV Crude Sample[e] | HAV Final Estimate[e] |
|---|---|---|---|---|---|---|---|---|
| 1 | $8.6 \times 10^5$ | $8.6 \times 10^2$ | 0.10 | $1.5 \times 10^8$ | $1.4 \times 10^8$ | 91.9 | ND[f] | — |
| 2 | $8.6 \times 10^5$ | $6.4 \times 10^2$ | 0.07 | $1.5 \times 10^8$ | $1.1 \times 10^8$ | 75.7 | $3.5 \times 10^1$ | $6.5 \times 10^4$ |
| 3 | $8.6 \times 10^5$ | $1.1 \times 10^3$ | 0.13 | $1.5 \times 10^8$ | $1.2 \times 10^8$ | 83.8 | ND | — |
| 4 | $8.6 \times 10^5$ | $1.3 \times 10^3$ | 0.15 | $1.5 \times 10^8$ | $1.3 \times 10^8$ | 89.2 | $1.1 \times 10^3$ | $7.3 \times 10^5$ |
| 5 | $8.6 \times 10^5$ | $8.0 \times 10^2$ | 0.09 | $1.5 \times 10^8$ | $9.6 \times 10^7$ | 64.8 | $4.4 \times 10^0$ | $7.5 \times 10^3$ |
| 6 | $8.6 \times 10^5$ | $5.9 \times 10^2$ | 0.07 | $1.5 \times 10^8$ | $1.2 \times 10^8$ | 78.4 | ND | — |
| 7 | $8.6 \times 10^5$ | $1.2 \times 10^3$ | 0.14 | $1.5 \times 10^8$ | $1.0 \times 10^8$ | 70.3 | ND | — |

[a]The inocula added are expressed as $TCID_{50}$/g of hepatopancreas.
[b]Each spiked sample was extracted and the nucleic acids suspension was titrated by real-time TaqMan RT-PCR using a standard curve made by means of Mengo virus infectious units.
[c]The inocula added are expressed as the number of molecules of the ssRNA control per ml of nucleic acids suspension.
[d]Each spiked nucleic acids suspension was titrated by a TaqMan Real-time RT-PCR using a standard curve made by means of HAV-derived ssRNA molecules estimated from the $OD_{260}$ readings.
[e]The titer is expressed as the number of genome copies per g of hepatopancreas.
[f]Not Detected (<6.66 copies per g of hepatopancreasor, assuming a 100% efficiency for both extraction and RT-PCR).

The invention claimed is:

1. A method of quantifying Hepatitis A virus in a sample, by real-time reverse transcription polymerase chain reaction (RT-PCR), comprising:
   (i) adding a known concentration of a Mengo virus to the sample, said Mengo virus being a mutant strain with the same growth properties as those of a wild-type Mengo virus and with no pathogenic capacity;
   (ii) performing a virus nucleic acids extraction of the sample to obtain a nucleic acids suspension;
   (iii) taking at least three subsamples of the nucleic acids suspension, here referred to as subsamples 1, 2 and 3;
   (iv) adding a known concentration of a single stranded RNA molecule corresponding to a fragment of the Hepatitis A virus genome to the subsample 1;
   (v) analyzing each of the subsamples 1, 2 and 3 by RT-PCR with a reaction mixture comprising:
   for subsamples 1 and 2, primers that specifically bind to 5' non coding regions of the Hepatitis A virus genome, and a detectable labeled probe that specifically binds to an amplimer of the Hepatitis A virus resulting from the RT-PCR, and,
   subsample 3, primers that specifically bind to regions of the Mengo virus that are appropriate to generate an amplimer of the Mengo virus and a detectable labeled probe that specifically binds to the amplimer of the Mengo virus resulting from the RT-PCR;
   (vi) determining concentrations in each of subsample 1, 2 and 3 by comparison of values obtained from the analysis in (v) with three standard curves, here referred to as standard curves 1, 2 and 3:
   standard curve 1 being used for quantification of the single stranded RNA molecule, and being made with the single stranded RNA molecule titrated by means of optical density;
   standard curve 2 being used for quantification of the Hepatitis A virus, and being made with a target amplimer titrated by means of optical density; and
   standard curve 3, being used for quantification of the Mengo virus, and being made with Mengo virus titrated by infectivity; and
   (vii) determining the efficiency of the RT-PCR by comparison of the number of single stranded RNA molecules detected, by subtracting the number of Hepatitis A virus genomes quantified in the subsample 2 from the sum of Hepatitis A virus plus single stranded RNA molecules in the subsample 1, with the number of single stranded RNA molecules added; and
   determining the efficiency of the nucleic acids extraction in step ii by comparison of the detected Mengo virus in the subsample 3 with the added Mengo virus.

2. The method according to claim 1, wherein the Mengo virus is the mutant strain vMC0, which lacks a poly(C) tract from the 5' non-coding region of the wild-type Mengo virus.

3. The method according to claim 1, wherein the primers for Hepatitis A virus comprise SEQ ID NO: 1-2.

4. The method according to claim 1, wherein the primers for Hepatitis A virus consist of SEQ ID NO: 1-2.

5. The method according to claim 1, wherein the probe for Hepatitis A virus comprises SEQ ID NO: 3.

6. The method according to claim 5, wherein the probe for Hepatitis A virus consists of SEQ ID NO: 3.

7. The method according to claim 1, wherein the primers for Mengo virus comprise SEQ ID NO: 8-9.

8. The method according to claim 7, wherein the primers for Mengo virus consist of SEQ ID NO: 8-9.

9. The method according to claim 1, wherein the probe for Mengo virus comprises SEQ ID NO: 10.

10. The method according to claim 9, wherein the probe for Mengo virus consists of SEQ ID NO: 10.

11. The method according to claim 1, wherein the detectable probes are labeled with fluorochromes.

12. The method according to claim 11, wherein the detectable probes are labeled with 6-carboxy-fluorescein (FAM) at the 5' end and are modified with a minor groove binder (MGB) at the 3' end.

13. The method according to claim 1, wherein the single strand RNA molecule corresponds to an amplimer from position 68 to 240 of the pHM175 43c strain of Hepatitis A virus with an added restriction site.

14. The method according to claim 1, wherein the target amplimer used for the standard curve 2 in step (vi) is a double stranded molecule corresponding to an amplimer of the Hepatitis A virus.

15. The method according to claim 1, wherein the optical density is measured at 260 nm.

16. The method according to claim 1, wherein the RT-PCR is performed in one step.

17. The method according to claim 16, wherein the RT-PCR is carried out under the following conditions:
   1 hour at 50° C. for the reverse transcription reaction,
   10 minutes at 95° C. as a hot start and
   45 cycles each of 15 seconds at 95° C. for denaturation, 1 minute at 60° C. for annealing and 1 minute at 70° C. for extension.

18. The method according to claim 1, wherein the sample is a clinical sample, and the concentration of Mengo virus added in (i) is around $10^5$ infectious units/ml.

19. The method according to claim 1, wherein the sample is shellfish, and the concentration of Mengo virus added in (i) is around $10^6$ infectious units/g.

20. The method according to claim 1, wherein the concentration of the single stranded RNA added in (iv) is around $10^8$ molecules/ml.

* * * * *